(12) United States Patent
Andersen et al.

(10) Patent No.: US 8,211,156 B2
(45) Date of Patent: Jul. 3, 2012

(54) OSTEOPORATIC SCREW AND EXPANSION SLEEVE

(76) Inventors: Bruce J. Andersen, Boise, ID (US); Christian G. Zimmerman, Boise, ID (US)

( * ) Notice: Subject to any disclaimer, the term of this patent is extended or adjusted under 35 U.S.C. 154(b) by 1196 days.

(21) Appl. No.: 12/020,230

(22) Filed: Jan. 25, 2008

(65) Prior Publication Data

US 2009/0192552 A1    Jul. 30, 2009

(51) Int. Cl.
*A61B 17/04*    (2006.01)
*A61B 17/84*    (2006.01)
*A61F 2/08*    (2006.01)
*F16B 13/06*    (2006.01)
*F16B 13/12*    (2006.01)

(52) U.S. Cl. ......... 606/309; 411/44; 411/80.5; 411/913
(58) Field of Classification Search .................. 606/303, 606/313, 300, 309, 310, 316; 411/18, 54, 411/54.1, 80.5, 913, 44

See application file for complete search history.

(56) References Cited

U.S. PATENT DOCUMENTS

| | | | | |
|---|---|---|---|---|
| 4,011,786 A | * | 3/1977 | Liebig | 411/60.2 |
| 4,475,856 A | * | 10/1984 | Toomingas | 411/33 |
| 4,930,963 A | * | 6/1990 | Rockenfeller et al. | 411/44 |
| 5,053,034 A | | 10/1991 | Olerud | |
| 5,057,109 A | | 10/1991 | Olerud | |
| 5,074,864 A | | 12/1991 | Cozad et al. | |
| 5,112,332 A | | 5/1992 | Cozad et al. | |
| 5,116,334 A | | 5/1992 | Cozad et al. | |
| 5,147,359 A | | 9/1992 | Cozad et al. | |
| 5,154,718 A | | 10/1992 | Cozad et al. | |
| 5,180,381 A | | 1/1993 | Aust et al. | |
| 5,603,713 A | | 2/1997 | Aust et al. | |
| 5,630,817 A | | 5/1997 | Rokegem et al. | |
| 5,870,870 A | * | 2/1999 | Utzman | 52/483.1 |
| 6,234,734 B1 | * | 5/2001 | Klippel | 411/42 |
| 6,457,922 B1 | * | 10/2002 | Tsai | 411/55 |
| 7,901,170 B2 | * | 3/2011 | Usui | 411/34 |
| 2001/0021852 A1 | * | 9/2001 | Chappius | 606/73 |
| 2002/0138076 A1 | | 9/2002 | Biedermann et al. | |
| 2004/0111088 A1 | | 6/2004 | Picetti et al. | |
| 2004/0153078 A1 | | 8/2004 | Grinberg | |

(Continued)

*Primary Examiner* — Thomas C. Barrett
*Assistant Examiner* — David Bates
(74) *Attorney, Agent, or Firm* — Robert L. Shaver; Dykas & Shaver, LLP

(57) ABSTRACT

The invention is a bone screw apparatus. The bone screw apparatus has two specialized functions for stabilizing the screw within a bone. The first is a mechanical structure that anchors the screw within a bone and the second is a structure that allows injection of bone cement through the screw assembly and into the interior structure of the bone. The anchoring mechanism functions by an expandable member that slides concentrically over the shaft of the screw. When the expandable member is forced over a portion of the screw shaft with an enlarged diameter, the expandable member extends radially from the screw shaft, and the bone screw is anchored to the interior structure of the bone. The injecting function of the bone screw apparatus functions through the use of a hollow core within the screw shaft. The hollow core of the screw shaft has an inlet at the top of the shaft and at least one outlet near the tip of the screw shaft. Once the screw shaft is inserted into the interior structure of a bone, bone cement may be injected into the inlet at the top of the screw shaft. The bone cement travels through the hollow core of the screw shaft and is extruded out the holes near the tip of the screw shaft. The bone cement fills the void spaces within the bone structure and strengthens the bone.

11 Claims, 6 Drawing Sheets

U.S. PATENT DOCUMENTS

| | | |
|---|---|---|
| 2006/0064090 A1 | 3/2006 | Park |
| 2006/0155278 A1 | 7/2006 | Warnick |
| 2006/0161153 A1 | 7/2006 | Hawkes et al. |
| 2006/0293693 A1 | 12/2006 | Farr et al. |
| 2007/0055238 A1 | 3/2007 | Biedermann et al. |
| 2010/0324607 A1* | 12/2010 | Davis .......................... 606/313 |

* cited by examiner

OSTEOPORATIC SCREW AND EXPANSION SLEEVE

FIELD OF THE INVENTION

The invention relates generally to a bone screw assembly and more particularly to a bone screw with an anchoring apparatus and a passage for injecting material into a bone.

BACKGROUND OF THE INVENTION

Bone screws have been known to the medical field for some time. Bone screws are used to bind fractured bone or attach therapeutic implants to bone structure. Placement of bone screws requires complicated and intricate surgical procedures.

Bone screws are common to spinal surgery in which adjacent vertebrae are linked together. The procedure of fusing vertebrae requires insertion of pedicle screws into the pedicle of vertebrae. Once the screws are set, separate hardware is used to link the screws in adjacent vertebrae together. The hardware is then tightened and the adjacent vertebrae are immobilized in relation to one another.

Problems often arise with conventional pedicle screws and the procedure of fusing vertebrae. Vertebrae are porous bone, especially in elderly patients. The lack of structural integrity in the bone often causes difficulty in maintaining pedicle screws in a fixed position in the vertebrae. Screws may work out of the vertebrae or crack and shatter regions of the vertebrae adjacent to the screw. Often, additional surgery is required to remedy problems arising from the use of conventional pedicle screws. Therefore, there exists a need for a pedicle screw with an anchoring mechanism and a means of stabilizing the structure of the vertebrae. The following invention addresses and provides a solution to these issues.

SUMMARY OF THE INVENTION

The invention is a bone screw assembly with an apparatus for anchoring the screw assembly within a bone and a hollow core structure for injecting fluid material into bone. The device contains a cylindrical screw shaft with a cutting tip on one end and a blunt driving tip on the other end. The surface of the screw shaft contains a helical groove that facilitates threading the screw shaft into the bone once the cutting tip of the screw is within the surface of the bone.

The anchoring function of the bone screw assembly is comprised of a number of parts that work together in order to anchor the bone screw assembly within a bone. The screw shaft has an enlarged bulb region in an intermediate portion of the surface of the screw shaft between the cutting tip and the blunt tip. The enlarged bulb separates the threaded helical groove of the screw shaft into two halves. The upper half contains the blunt driving tip of the screw shaft, and a lower half of the screw shaft contains the cutting tip. The diameter of the enlarged bulb is greater than the other portions of the screw shaft. The anchoring assembly also includes two separate tubular sleeves that fit adjacent to one another on the upper half of the screw shaft. The two tubular sleeves are arranged on the screw shaft so that one tubular sleeve concentrically encloses the upper half of the screw shaft adjacent the enlarged bulb and the other tubular sleeve concentrically encloses a separate portion of the upper half of the screw shaft adjacent to the first sleeve.

The first sleeve concentrically enclosing the upper half of the screw shaft is an expandable collar. One end of the expandable collar expands radially outward when force is applied from the interior of the expandable collar. The opposite end of the expandable collar is a continuous tube. The expandable collar fits concentrically onto the upper half of the screw shaft so the expandable portion of the expandable collar is oriented adjacent to the enlarged bulb. The second sleeve concentrically enclosing the upper half of the screw shaft is a bushing. The bushing fits concentrically around the upper half of the screw shaft in a region between the expandable collar and the blunt driving tip of the screw shaft. Both ends of the bushing are in the shape of a continuous tube.

A tightening nut is placed near the end of the upper half of the screw shaft. The tightening nut has a hollow and threaded tunnel which mates with the helically grooved portion of the upper half of the screw shaft. The tightening nut has two functioning sides. The first side engages the bushing on the upper half of the screw when the tightening nut is threaded onto the upper half of the screw shaft. The second side of the tightening nut contains an adjustment and attachment interface for rotating the tightening nut and for connecting additional hardware to the bone screw assembly once it is anchored.

The anchoring mechanism is deployed by boring a hole in a bone and inserting the cutting tip of the screw shaft within the bone. Once the hole is created, the lower half of the screw shaft is threaded into the bone until the enlarged bulb and the slotted end of the expandable collar are within the interior structure of the bone. The tightening nut is then threadably twisted about the helical grooves on the upper half of the screw shaft. Rotating the tightening nut in this manner forces the bushing and the expandable collar toward the enlarged bulb. The expandable portion of the expandable collar is forced over the expandable bulb, forcing the expandable portion of the collar radially outward and into the bone structure, thereby anchoring the bone screw assembly within the bone.

The injection mechanism of the bone screw assembly functions through a hollow axial core that extends the length of the screw shaft from the cutting tip on one end of the screw shaft to the blunt driving tip on the other end of the screw shaft. The hollow axial core has at least one opening near the cutting tip and one opening at the blunt driving tip on the other end of the screw shaft. These openings are passages that access the hollow axial core of the screw shaft from the surface of the screw shaft. The openings allow a fluid material to be injected into the bone through the bone screw assembly.

The injection function of the bone screw assembly allows the injection of a fluid material into the interior of a bone. The process of injecting the material is achieved by first boring a hole in the surface of the bone and inserting the cutting tip of the screw shaft into the bone. Once the initial hole is bored into the bone, the lower half of the screw shaft is threaded into the bone until at least one of the openings in the lower half of the screw shaft is within the interior of the bone. Again, these openings lead from the hollow axial core of the screw shaft to the surface of the screw shaft. Once the screw assembly has been positioned in this manner, a fluid material is injected into the opening within the blunt driving tip of the screw shaft. The fluid material travels through the hollow axial core of the screw shaft and is extruded out the opening or openings of the lower half of the screw shaft within the interior of the bone. The fluid material then fills the void spaces within the interior of the bone.

The purpose of the foregoing Abstract is to enable the public, and especially the scientists, engineers, and practitioners in the art who are not familiar with patent or legal terms or phraseology, to determine quickly from a cursory inspection, the nature and essence of the technical disclosure of the application. The Abstract is neither intended to define the invention of the application, which is measured by the claims, nor is it intended to be limiting as to the scope of the invention in any way.

Still other features and advantages of the present invention will become readily apparent to those skilled in this art from the following detailed description describing preferred embodiments of the invention, simply by way of illustration of the best mode contemplated by carrying out my invention. As will be realized, the invention is capable of modification in various obvious respects all without departing from the invention. Accordingly, the drawings and description of the preferred embodiments are to be regarded as illustrative in nature, and not as restrictive in nature.

DESCRIPTION OF THE PREFERRED EMBODIMENTS

Figure 1:
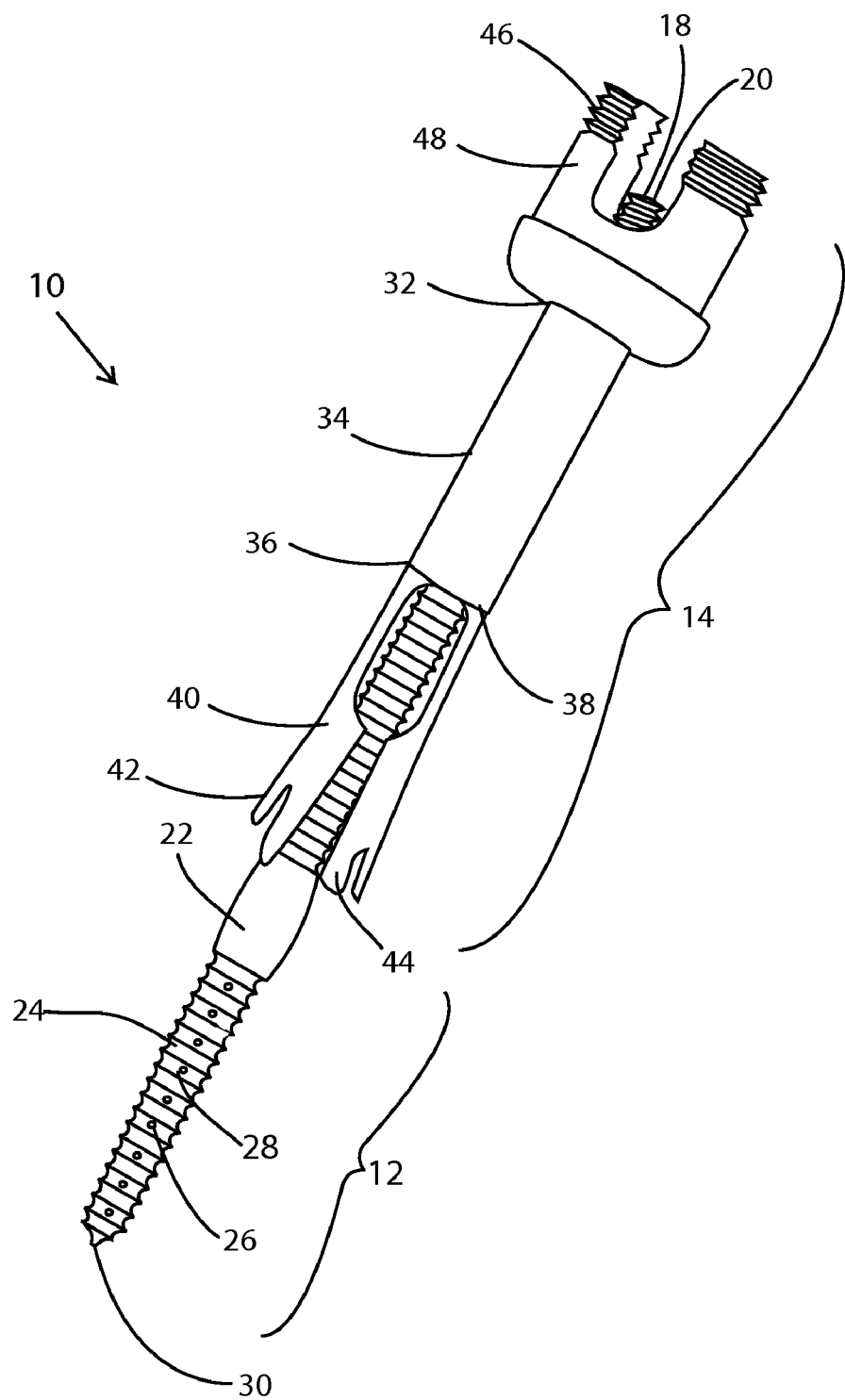
FIG. 1 is a perspective view of the bone screw assembly with the anchoring mechanism retracted.

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

The field art related to bone screws, pedicle screws in particular, has seen a long felt and unresolved need for a bone screw that anchors within a vertebrae and stabilizes the vertebrae. Bone material in vertebrae is porous material, especially in elderly patients. Therefore, conventional pedicle screws often become dislodged or shatter bone material in the vertebrae due to lack of structural stability within the bone. When pedicle screws become dislodged in this manner, additional surgery is required to remedy the problem. It is undesirable for screws to become dislodged and create bone fragmentation in the critical and sensitive region of the spinal column. The invention described below, addresses and provides a solution to the problems previously encountered with conventional pedicle screws.

The present invention is a bone screw assembly with an anchoring mechanism and an apparatus designed for injecting stabilizing material into the interior of a bone. The anchoring mechanism of the bone screw assembly consists of a number of moving parts that function to deploy a mechanical anchoring structure from the bone screw to the interior of a bone. The bone screw assembly has a hollow axial core that facilitates the injection of a bone stabilizing cement into the interior of a bone through the structure of the bone screw. The invention solves the problems related to setting bone screws in unstable bone material, through the use of a mechanical anchoring apparatus and a structure for injecting a stabilizing material into the bone through the hollow bone screw assembly.

In the following description and in the figures, like elements are identified with like reference numerals. The use of "or" indicates a non-exclusive alternative without limitation unless otherwise noted. The use of "including" means "including, but not limited to," unless otherwise noted.

FIG. 1 illustrates a perspective view of the assembled bone screw assembly 10. A number of the components and the structure of the bone screw assembly are displayed in FIG. 1. A portion of the cylindrical screw shaft 12 is visible. The screw shaft 12 runs the entire length of the bone screw assembly. The lower half 28 of the screw shaft 12 is visible in FIG. 1. The end of the lower half 28 of the screw shaft 12 is a cutting tip 30. The cutting tip 30 has a right circular conical structure that is tapered to a point from the cylindrical screw shaft 12. A lower helical groove 24, formed into the surface of the lower half 28 of the screw shaft 12, extends from the cutting tip 30 of the screw shaft 12 to the enlarged bulb 22. The enlarged bulb 22 lies approximately halfway between the ends of the screw shaft 12, and has a greater diameter than the other portions of the screw shaft 12. The enlarged bulb 22 is discussed in more detail in paragraphs below.

Also illustrated in FIG. 1 is a series of fluid material outlet pores 26 within the lower helical groove 24 of the screw shaft 12. The fluid material outlet pores 26 are discussed in greater detail in paragraphs below regarding the process of injecting bone cement into the interior cavities of a bone. FIG. 1 additionally illustrates an expandable collar 40, a bushing 34, and a tightening nut 48, all of which are illustrated on the upper half 14 of the screw shaft 12. The expandable collar 40, bushing 34, and tightening nut 48 are components of the bone screw anchoring mechanism that is discussed in detail in paragraphs below. Also illustrated in FIG. 1 is the blunt tip 18 of the screw shaft. The blunt tip 18 of the screw shaft resides on the opposite end of the screw shaft 12 from the cutting tip 30. The blunt tip 18 contains an opening that serves as the fluid material injection inlet 20. The fluid material injection inlet 20 serves an access point for feeding bone cement into the bone screw assembly 10 when injecting the cement into the interior of a bone.

Figure 2:
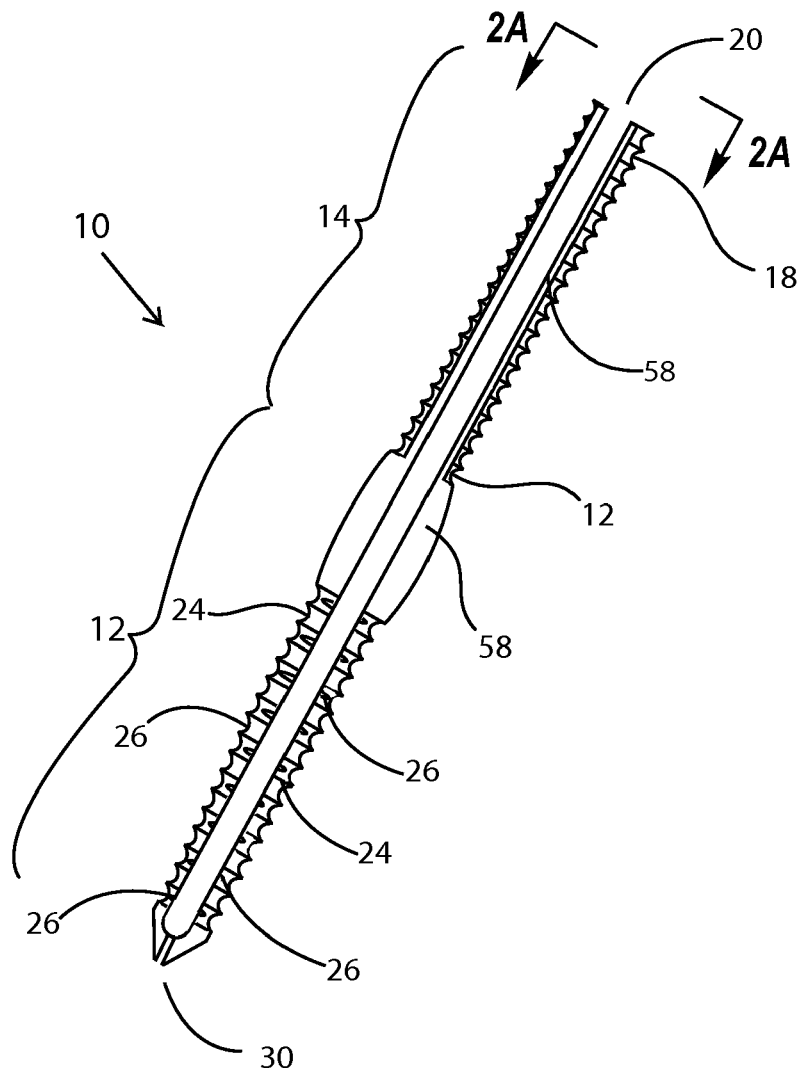
FIG. 2 is a cross-section view of the screw shaft, illustrating the hollow axial core of the screw shaft.
Figure 2A:
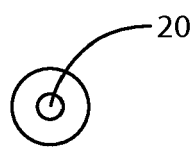

FIG. 2 illustrates a cross-section of the screw shaft 12, and a hollow axial core 58 within the interior of the screw shaft. The hollow axial core 58 extends from the blunt tip 18 of the upper half 14 of the screw shaft 12 to the cutting tip 30 of the lower half 28 of the screw shaft 12. The fluid material injection inlet 20 accesses the hollow axial core at the blunt tip of the screw shaft. A series of fluid material outlet pores 26 are formed within the lower helical groove 24 of the lower half 28 of the screw shaft 12. The hollow axial core allows passage of injected material from the fluid material injection inlet 20 to the fluid material outlet pores 26.

Figure 3:
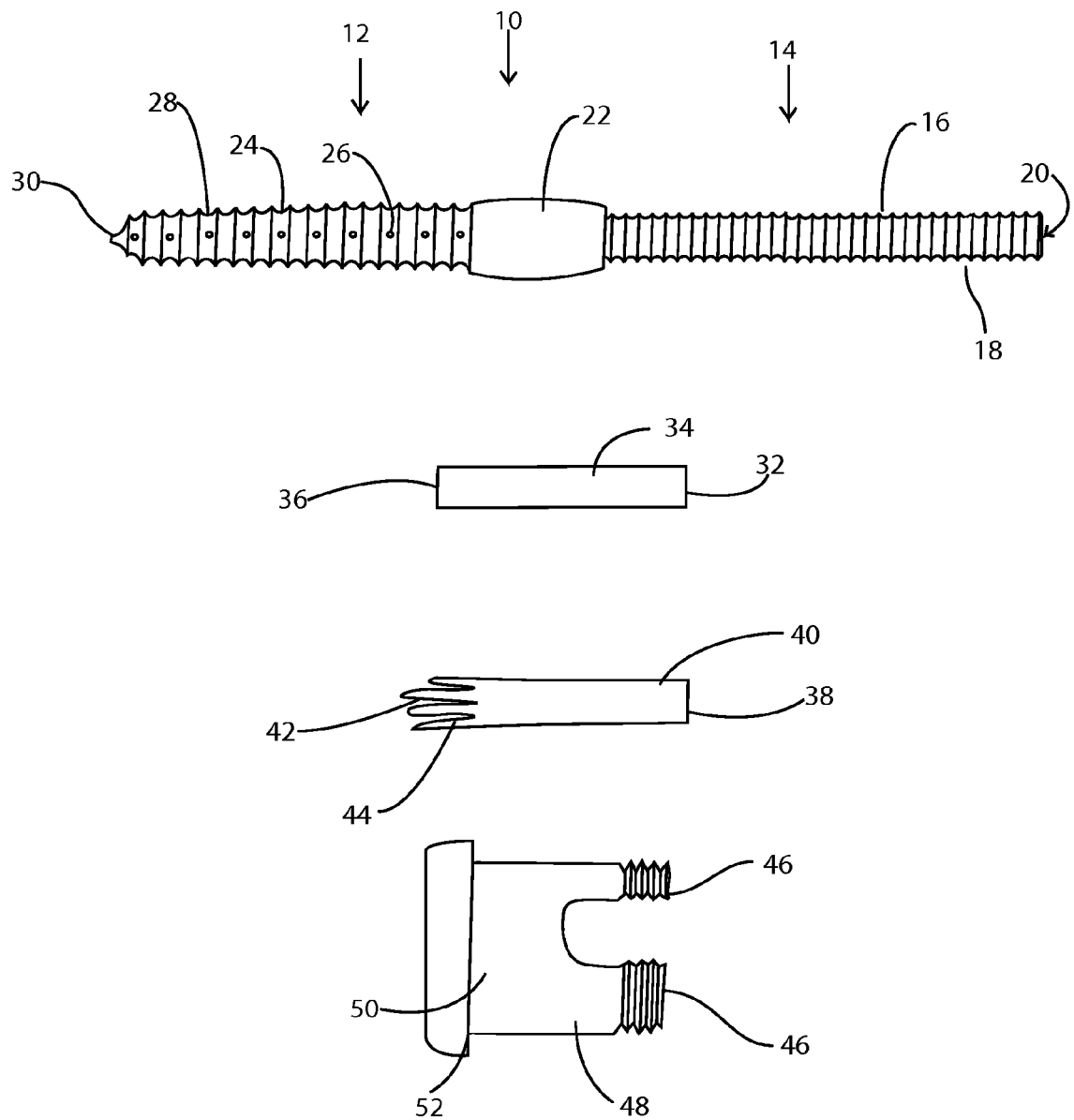
FIG. 3 is a disassembled view of the bone screw assembly.

FIG. 3 illustrates a disassembled view of the component parts of the bone screw assembly 10. The parts in FIG. 3 include the screw shaft 12, which has an upper half 14 and a lower half 28 separated by an enlarged bulb 22. The enlarged bulb 22 has a greater diameter than the other portions of the screw shaft 12, and serves as a key functioning element of the anchoring mechanism. Clearly visible in FIG. 3 is the upper half 14 of the screw shaft 12, which contains the upper helical grooves 16. Unlike the lower helical grooves 24, the upper helical groove 16 contains no fluid material outlet pores.

FIG. 3 also illustrates the separable portions of the bone screw anchoring assembly. The expandable collar 40 is illustrated disconnected from the screw shaft 12. The expandable collar 40 has a cylindrical structure that fits concentrically around the upper half 14 of the screw shaft 12. A first end of the expandable collar 40 has a series of prongs 44 around the periphery of the expandable collar's tubular structure. The prongs 44 are separated by a series of slots 42. The second end 38 of the expandable collar 40 is a continuous, circular, tubular end with no prongs or slots.

FIG. 3 also illustrates the bushing 34. The bushing 34 is the same diameter as the expandable collar and has a similar tubular structure. However, the bushing 34 is a continuous, circular, tubular, cylinder from end to end. The bushing contains a smooth tubular first end 36 and a smooth tubular second end 32. The bushing also fits concentrically around the upper half 14 of the screw shaft 12.

FIG. 3 additionally illustrates a tightening nut 48. The tightening nut has a threaded tunnel 50 that threads onto the upper helical groove 16 of the upper half 14 of the screw shaft 12. The tightening nut 48 has smooth bushing engagement face 52 with an opening to the threaded tunnel 50. The opposite side of the tightening nut 48 has an adjustment and attachment interface 46 that is used to twist the tightening nut 48 onto the upper half 14 of the screw shaft 12. The adjustment and attachment interface may also be used to attach the bone screw assembly 10 to additional surgical hardware.

The process of deploying the anchoring mechanism requires that the bone screw assembly 10 must be inserted into a bone with the anchoring assembly retracted. The correct structure of the bone screw assembly 10 with the anchoring assembly retracted is illustrated in FIG. 1. In retracted orientation, the expandable collar 40 is concentrically fitted over the upper half 14 of the screw shaft 12. The pronged end 44 of the expandable collar is adjacent and nearest the enlarged bulb 22 while remaining retracted on the upper half of the screw shaft. The second end 38 of the expandable collar is also positioned concentrically about the upper half 14 of the screw shaft 12 in an intermediate region between the blunt tip 18 of the screw shaft 12 and the pronged end 44 of the expandable collar which is adjacent the enlarged bulb 22. The bushing 34 fits concentrically about the upper half 14 of the screw shaft 12 so that the first end 36 of the bushing 34 contacts the second end 38 of the expandable collar 40. The second end 32 of the bushing 34 concentrically lies proximal to the blunt tip 18 of the upper half 14 of the screw shaft 12. A portion of the upper helical groove 16 remains exposed between the blunt tip 18 of the screw shaft 12 and the second end 32 of the bushing 34. The tightening nut 48 is threaded onto exposed portion of the upper helical groove 16 on the upper half 14 of the screw shaft 12 so that the bushing engagement face 52 of the tightening nut 48 contacts the second end 32 of the bushing 34.

The process of deploying the bone anchoring structure of the bone screw assembly 10 requires boring a hole in the surface of a bone. The cutting tip 30 and the lower half 28 of the screw shaft 12 are threaded into the bone with the use of the lower helical grooves 24. The screw shaft 12 is inserted into the bone until the enlarged bulb 22 and the pronged ends 44 of the expandable collar 40 are within the interior of the bone. The anchoring mechanism may be deployed when the bone screw assembly is at this depth within the bone.

Figure 4:
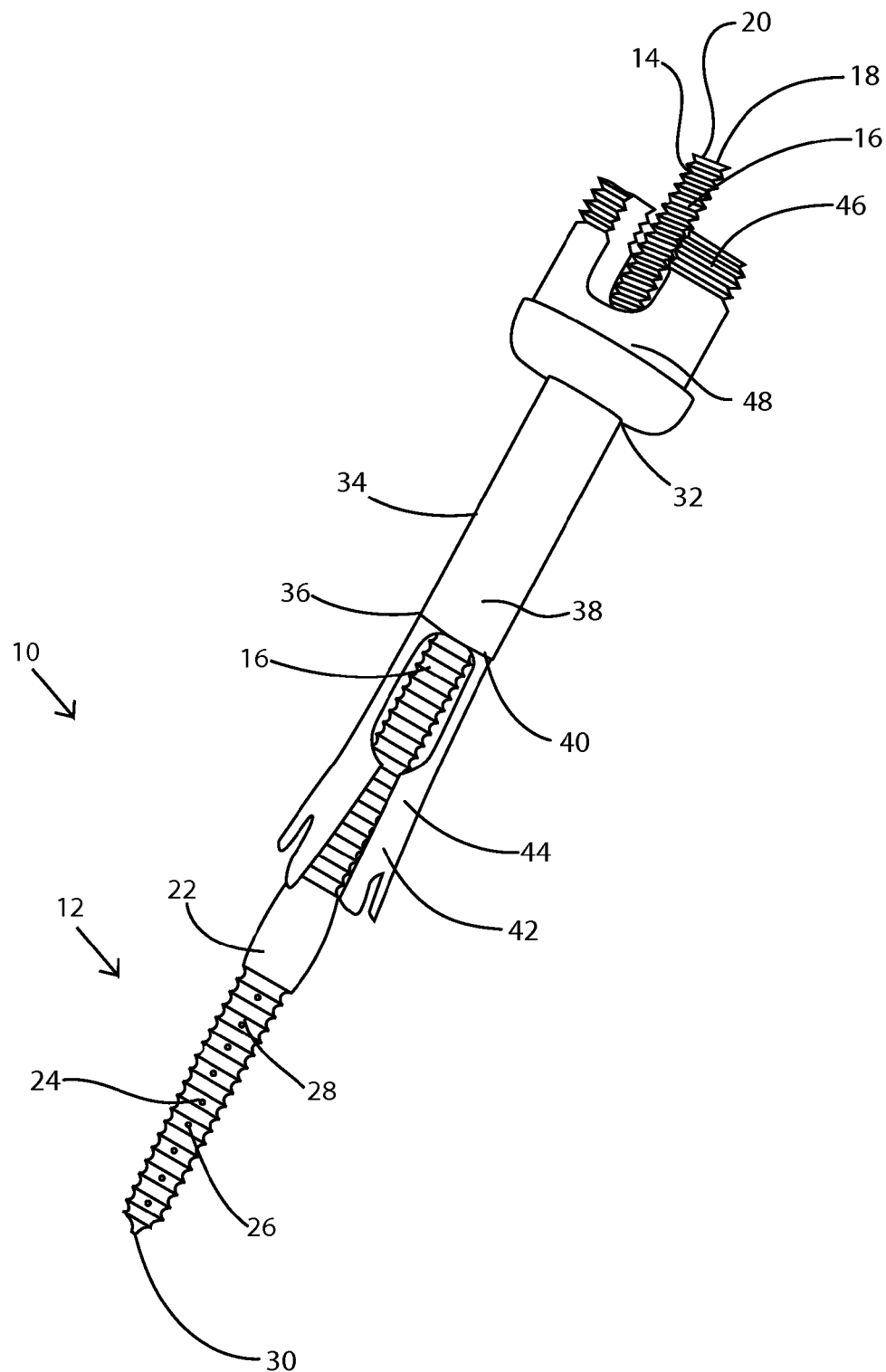
FIG. 4 is a perspective view of the assembled bone screw assembly with the anchoring mechanism extended.

FIG. 4 illustrates the bone screw assembly 10, with the anchoring mechanism deployed. Deploying the anchoring structure is accomplished by rotating the tightening nut 48 about the upper half 14 of the screw shaft 12, so that the threaded tunnel 50 of the tightening nut 48 travels the upper helical groove 16 in the direction of the enlarged bulb 22. The bushing engagement face 52 of the tightening nut 48 forces the bushing 34 in the direction of the enlarged bulb 22, which in turn forces the expandable collar 40 in the direction of the enlarged bulb 22. The pronged ends 44 of the expandable collar 40 are thereby forced over the periphery of the enlarged bulb 22. This forces the prongs 44 radially outward and into the structure of the bone, thereby anchoring the bone screw assembly 10 within the bone.

Figure 5:
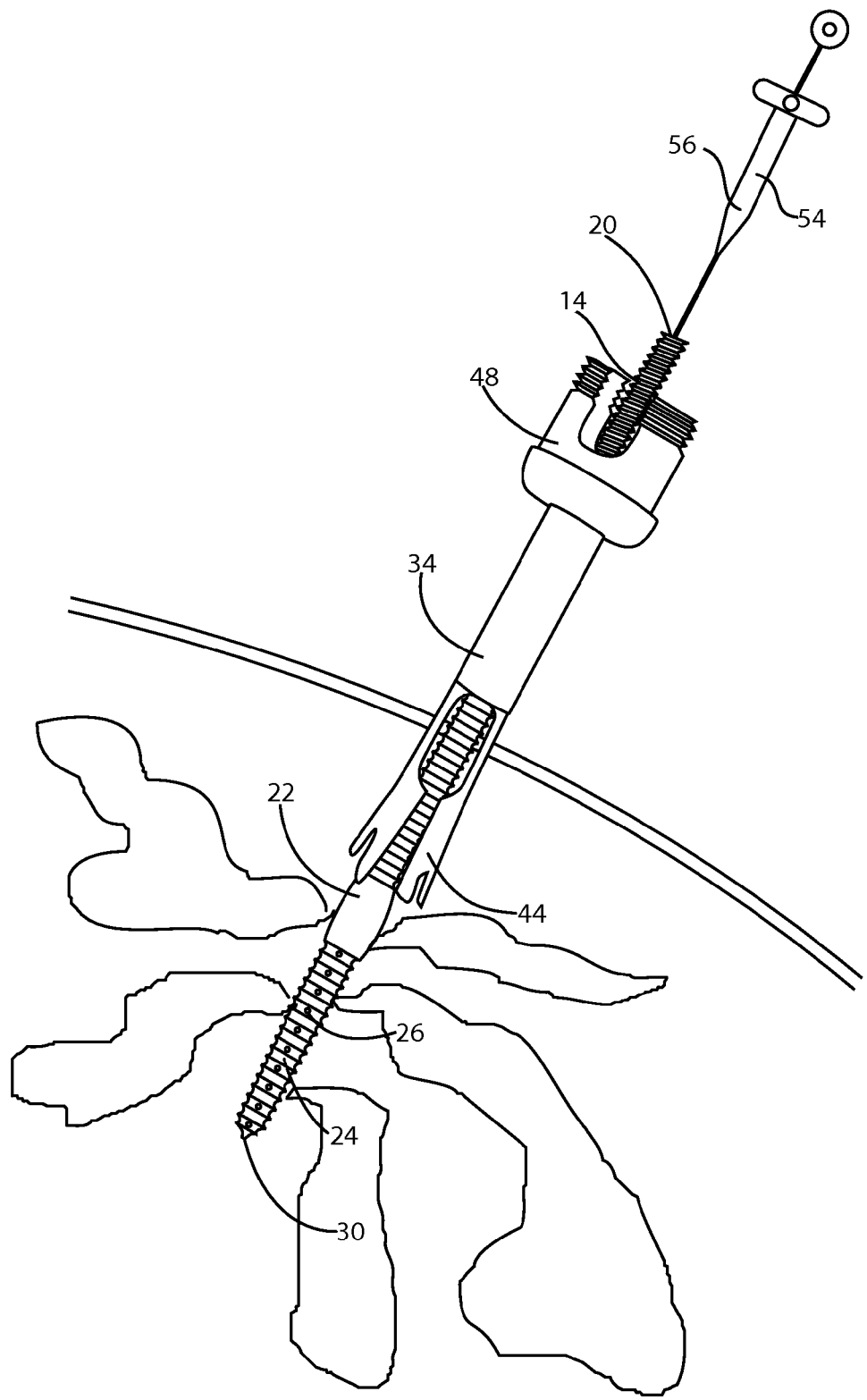
FIG. 5 illustrates the bone screw assembly inserted into a cross-section of bone, with bone cement being injected into bone through the bone screw assembly.
Figure 6:
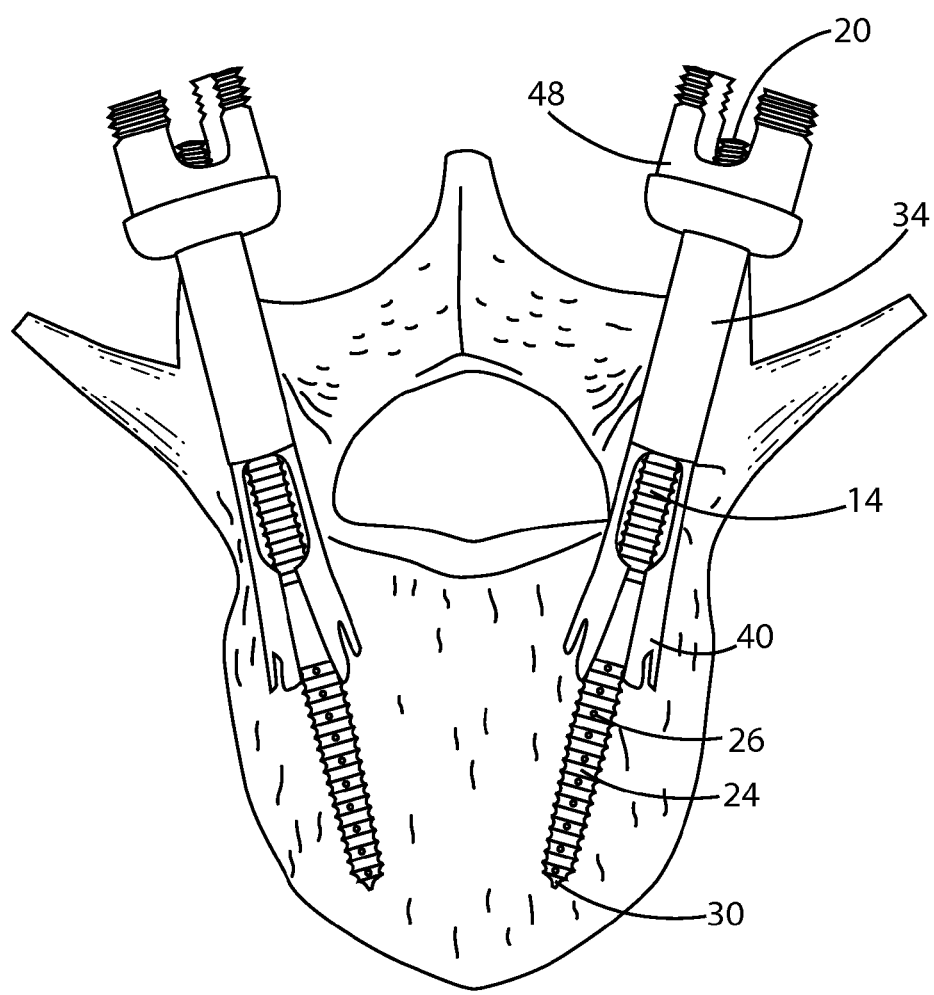
FIG. 6 is a cross sectional view of the device mounted in bone.

FIG. 5 illustrates the bone screw assembly inserted into a bone with the anchoring mechanism deployed within the bone. FIG. 5 also illustrates the injection capability of the bone screw assembly. The figure illustrates a syringe 54 injecting bone cement 56 into the fluid material injection inlet 20. When injected, the bone cement 56 travels through the interior axial core of the screw shaft 12 to the lower half 28 of the screw shaft 12 and extrudes through the fluid material outlet pores 26 within the lower helical grooves 24 of the screw shaft 12. The bone cement 56 then fills the porous void spaces within the interior of the bone structure. When the bone cement 56 solidifies, the bone is strengthened.

The exemplary embodiments shown in the figures and described above illustrate but do not limit the invention. It should be understood that there is no intention to limit the invention to the specific form disclosed; rather, the invention is to cover all modifications, alternative constructions, and equivalents falling within the spirit and scope of the invention as defined in the claims. For example, while the exemplary embodiments illustrate an osteoporatic screw and molly bolt, the invention is not limited to use as a pedicle screw and may be used with other bones or for other uses. While the invention is not limited to use as a pedicle screw, it is expected that various embodiments of the invention will be particularly useful in such devices. Hence, the foregoing description should not be construed to limit the scope of the invention, which is defined in the following claims.

While there is shown and described the present preferred embodiment of the invention, it is to be distinctly understood that this invention is not limited thereto but may be variously embodied to practice within the scope of the following claims. From the foregoing description, it will be apparent that various changes may be made without departing from the spirit and scope of the invention as defined by the following claims.

What is claimed is:

1. A bone screw assembly with an anchoring apparatus and an injection apparatus, comprising:

a screw shaft having a first end and a second end;

an enlarged bulb, said enlarged bulb positioned in an intermediate region of said screw shaft between said first end of said screw shaft and said second end of said screw shaft, said enlarged bulb having a greater diameter than the remainder of said screw shaft, said enlarge bulb fixed in position between said first end and said second end of said screw shaft;

a first half of said screw shaft between said first end of said screw shaft and said enlarged bulb;

a second half of said screw shaft between said second end of said screw shaft and said enlarged bulb;

a first set of helical grooves on the surface of said first half of said screw shaft, said first set of helical grooves located between said first end of said screw shaft and said enlarged bulb;

an anchor engagement structure on the surface of said second half of said screw shaft, said anchor engagement structure located between said second end of said screw shaft and said enlarged bulb;

a hollow axial core within said screw shaft; said hollow axial core of said screw shaft having at least one opening in said first end of said screw shaft, and said hollow axial core of said screw shaft having an opening in said second end of said screw shaft;

an expandable collar with a first end and a second end, said expandable collar having a tubular structure, said expandable collar fitting concentrically over said screw shaft, said first end of said expandable collar having radially expandable portion, said first end of said expandable collar capable of expansion in multiple radial directions with application of outward radial force from the center axis of said expandable collar, said second end of said expandable collar having a tubular structure, said expandable collar configured to expand upon contact with said enlarged bulb when said expandable collar is moved toward said enlarged bulb, and configured to penetrate surrounding bone tissue upon radial expansion;

a bushing with a first end and a second end, said first end of said bushing having a tubular structure, said second end of said bushing having a tubular structure, said bushing fitting concentrically over said screw shaft;

a tightening nut having a first side and a second side, a tunnel through the body of said tightening nut, said tunnel opening on said first side and said second side of said tightening nut, said tunnel shaped to surround said second half of said screw shaft, said interior surface of said tunnel having a structure capable of engaging said anchor engagement structure of said second half of said screw shaft and by pushing against said bushing, pushing said expandable collar toward said enlarged bulb, said first side of said tightening nut having a bushing engagement face, said second side of said tightening nut having an adjustment and attachment interface, said adjustment and attachment interface having a structure for grasping and adjustment of tightening nut, and said adjustment and attachment interface having regions for attaching additional hardware to said bone screw assembly; and said bone screw assembly assembled with said expandable collar oriented concentrically around said second half of said screw shaft with said first end of said expandable collar adjacent to said enlarged bulb and said second end of said expandable collar positioned in an intermediate region between said enlarged bulb and said second end of said screw shaft, said bushing oriented concentrically around said screw shaft with said first end of said bushing adjacent to said second end of said expandable collar and said second end of said bushing proximal to said second end of said screw shaft, said tunnel of said tightening nut surrounding a portion of said second half of said screw shaft, said first side of said tightening nut positioned adjacent to said second end of said bushing, said adjustment and attachment interface of said tightening nut adjacent to said second end of said screw shaft.

2. The bone screw assembly of claim 1 wherein said screw shaft is a cylindrical screw shaft.

3. The bone screw assembly of claim 1 wherein said first end of said screw shaft is a right circular, conical cutting tip.

4. The bone screw assembly of claim 1 wherein said second end of said screw shaft is a blunt tip.

5. The bone screw assembly of claim 1 wherein said first half of said screw shaft contains a porous screw structure, said porous screw structure comprising pores extending radially from said hollow axial core of said first half of said screw shaft to the surface of said first half of said screw shaft, for injection of bone cement into a region around said first end of said screw shaft.

6. The bone screw assembly of claim 1 wherein said expandable collar has a slotted first end, said slotted first end having prongs capable of being forced radially outward from the center axis of said expandable collar.

7. The bone screw assembly of claim 1 wherein said anchor engagement structure comprises second set of helical grooves.

8. The bone screw assembly of claim 7 wherein said tightening nut contains a tunnel with a structure that threads onto said second set of helical grooves.

9. A bone screw assembly with an anchoring apparatus and an injection apparatus, comprising:

a screw shaft having a first end and a second end;

an enlarged bulb, said enlarged bulb positioned in an intermediate region of said screw shaft between said first end of said screw shaft and said second end of said screw shaft, said enlarged bulb having a greater diameter than the remainder of said screw shaft;

a first half of said screw shaft between said first end of said screw shaft and said enlarged bulb;

a second half of said screw shaft between said second end of said screw shaft and said enlarged bulb;

a first set of helical grooves on the surface of said first half of said screw shaft, said first set of helical grooves located between said first end of said screw shaft and said enlarged bulb;

an anchor engagement structure on the surface of said second half of said screw shaft, said anchor engagement structure located between said second end of said screw shaft and said enlarged bulb;

a hollow axial core within said screw shaft; said hollow axial core of said screw shaft having at least one opening in said first end of said screw shaft, and said hollow axial core of said screw shaft having an opening in said second end of said screw shaft for injection of bone cement;

an expandable collar with a first end and a second end, said expandable collar having a tubular structure, said expandable collar fitting concentrically over said screw shaft, said first end of said expandable collar having radially expandable portion, said first end of said expandable collar capable of expansion in multiple radial directions with application of outward radial force from the center axis of said expandable collar, said second end of said expandable collar having a tubular structure;

a bushing with a first end and a second end, said first end of said bushing having a tubular structure, said second end of said bushing having a tubular structure, said bushing fitting concentrically over said screw shaft;

a tightening nut having a first side and a second side, a tunnel through the body of said tightening nut, said tunnel opening on said first side and said second side of said tightening nut, said tunnel shaped to surround said second half of said screw shaft, said interior surface of said tunnel having a structure capable of engaging said anchor engagement structure of said second half of said screw shaft, said first side of said tightening nut having a bushing engagement face, said second side of said tightening nut having an adjustment and attachment interface, said adjustment and attachment interface having a structure for grasping and adjustment of tightening nut, and said adjustment and attachment interface having regions for attaching additional hardware to said bone screw assembly; and said bone screw assembly assembled with said expandable collar oriented concentrically around said second half of said screw shaft with said first end of said expandable collar adjacent to said enlarged bulb and said second end of said expandable collar positioned in an intermediate region between said enlarged bulb and said second end of said screw shaft, said bushing oriented concentrically around said screw shaft with said first end of said bushing adjacent to said second end of said expandable collar and said second end of said bushing proximal to said second end of said screw shaft, said tunnel of said tightening nut surrounding a portion of said second half of said screw shaft, said first side of said tightening nut positioned adjacent to said second end of said bushing, said adjustment and attachment interface of said tightening nut adjacent to said second end of said screw shaft; wherein said anchor engagement structure comprises a series of ratchet teeth.

10. The bone screw assembly of claim 9 wherein said tightening nut contains a tunnel with a ratchet mechanism that threads onto said ratchet teeth.

11. A bone screw assembly with an anchoring means and an injection means, said bone screw assembly comprising:
- a screw shaft, said screw shaft having a first end and a second end, said screw shaft having a cylindrical shape, said first end of said screw shaft having a cutting tip, said second end of said screw shaft having a blunt tip;
- an enlarged bulb formed within a substantially intermediate region of said screw shaft between said first end and said second end of said screw shaft, said enlarged bulb having a greater diameter than said screw shaft and being fixed in position between said first end and said second end of said screw shaft;
- a first helically grooved portion of the screw shaft extending from said cutting tip of said first end of said screw shaft to said enlarged bulb, said first helically grooved portion being the first half of said screw shaft,
- a second helically grooved portion of the screw shaft extending from said enlarged bulb to said blunt tip of said second end of said screw shaft, said second helically grooved portion being the second half of said screw shaft;
- a hollow axial core within said screw shaft, said hollow axial core having at least one opening on said first half of said screw shaft, and said hollow axial core having an opening in the second end of said screw shaft for injection of bone cement into said screw shaft and into an area adjacent to said first end of said screw shaft;
- an expandable collar, said expandable collar having a tubular structure, said expandable collar fitting concentrically around said screw shaft, said expandable collar having a first end and a second end, said first end of said expandable collar being slotted with prongs, said prongs capable of expansion with outward radial force from the axis of said screw shaft when said expandable collar is pressed against said enlarged bulb, said second end of said expandable collar being a continuous non-expandable tube;
- a bushing, said bushing having a tubular structure, said bushing having a first end and a second end;
- a tightening nut, said tightening nut having an tunnel threaded to mate with said second helically grooved portion of said second half of said screw shaft, said tightening nut having a first side and a second side, said tunnel through said tightening nut opening on said first and second sides of said tightening nut, said first side of said tightening nut having a planar engagement structure, said second side have a tightening and attachment structure;
- an assembled configuration of said bone screw apparatus comprising orientation of said expandable collar concentrically on said second half of said screw shaft, said first slotted end of said expandable collar positioned adjacent to said enlarged bulb formed in said screw shaft and configured to expand when pressed against said enlarge bulb, said second end of said expandable collar positioned in a substantially intermediate region of said second half of said screw shaft between said enlarged bulb and said blunt tip of said screw shaft; said bushing positioned concentrically around said second half of said screw shaft, said first end of said bushing adjacent to said second end of said expandable collar and said bushing configured to press said expandable collar against said enlarged bulb, said second end of said bushing proximal to said blunt tip of said screw shaft, said tightening nut concentrically threaded on said second half of said screw shaft, said first side of said tightening nut adjacent to said second end of said bushing, said second side of said tightening nut adjacent to said blunt tip of said screw shaft, and tightening nut configured to press said bushing against said expandable collar.

* * * * *